(12) United States Patent
Harris et al.

(10) Patent No.: US 7,678,077 B2
(45) Date of Patent: Mar. 16, 2010

(54) VARIABLE DEPTH INJECTION DEVICE AND METHOD

(75) Inventors: Chad G. Harris, Albertsville, MN (US); Matthew L. Hawk, Otsego, MN (US); Timothy J. Mickley, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1420 days.

(21) Appl. No.: 10/781,775

(22) Filed: Feb. 20, 2004

(65) Prior Publication Data

US 2005/0187519 A1    Aug. 25, 2005

(51) Int. Cl.
*A61M 5/00*    (2006.01)

(52) U.S. Cl. .................. 604/117; 604/44; 604/46; 604/108; 604/109; 604/158; 604/164.01; 604/165.01; 604/165.02; 604/264; 604/272; 606/172

(58) Field of Classification Search .............. 604/19, 604/21–22, 27, 43–44, 46, 93.01, 103.09, 604/108–109, 116–117, 158–159, 160–162, 604/164.01, 164.06–164.09, 164.11–164.12, 604/165.01–165.02, 166.01, 172–173, 264, 604/272, 523, 527–528; 606/1, 167, 172; 600/433–435, 564, 585
See application file for complete search history.

(56) References Cited

U.S. PATENT DOCUMENTS

| | | | |
|---|---|---|---|
| 3,750,667 A * | 8/1973 | Pshenichny et al. ........ 604/117 |
| 4,645,491 A | 2/1987 | Evans et al. |
| 4,710,171 A | 12/1987 | Rosenberg et al. |
| 4,763,667 A * | 8/1988 | Manzo ................. 600/563 |
| 5,009,637 A * | 4/1991 | Newman et al. .......... 604/68 |
| 6,083,222 A | 7/2000 | Klein et al. |
| 6,238,406 B1 | 5/2001 | Ellis et al. |
| 6,254,573 B1 | 7/2001 | Haim et al. |
| 6,258,064 B1 * | 7/2001 | Smith et al. ........... 604/164.12 |
| 6,540,725 B1 * | 4/2003 | Ponzi .................. 604/272 |
| 6,595,958 B1 | 7/2003 | Mickley |
| 6,613,017 B1 * | 9/2003 | Mickley .............. 604/117 |
| 6,616,626 B2 * | 9/2003 | Crank et al. ............ 604/48 |
| 2002/0082546 A1 | 6/2002 | Crank et al. |
| 2003/0014010 A1 | 1/2003 | Carpenter et al. |

FOREIGN PATENT DOCUMENTS

| | | |
|---|---|---|
| EP | 1205 207 A1 | 5/2002 |
| WO | 02-011807 A2 | 2/2002 |
| WO | WO 02/11808 A2 | 2/2002 |

* cited by examiner

*Primary Examiner*—Nicholas D Lucchesi
*Assistant Examiner*—Quynh-Nhu H Vu
(74) *Attorney, Agent, or Firm*—Vidas, Arrett & Steinkraus P.A.

(57) ABSTRACT

An apparatus for the injection of therapeutic and other agents at a target site within a patient's body. A catheter including a first elongated shaft having a distal end and a proximal end and a lumen extending therebetween. The catheter also including a second elongated shaft slidingly disposed in the first elongated shaft, the second elongated shaft having a distal end and a proximal and a lumen extending therebetween. The catheter further including a third elongated shaft disposed in and attached to the second elongate shaft, the third elongated shaft to move in a one-to-one relationship with the first elongated shaft and the second elongated shaft to maintain a predetermined needle deployment length as each are subjected to various bend configurations.

7 Claims, 8 Drawing Sheets

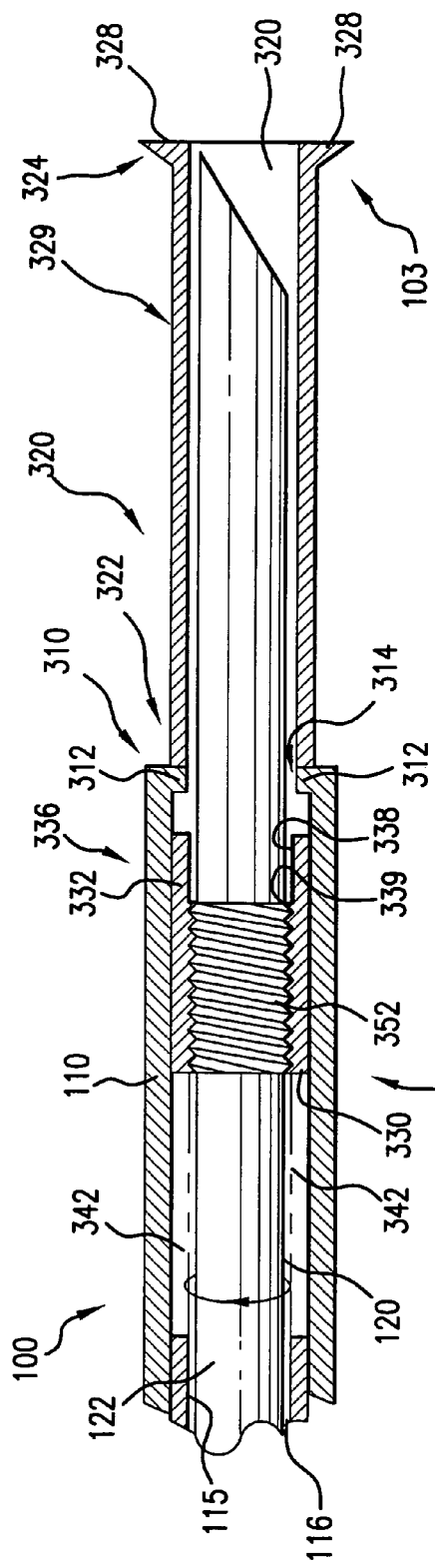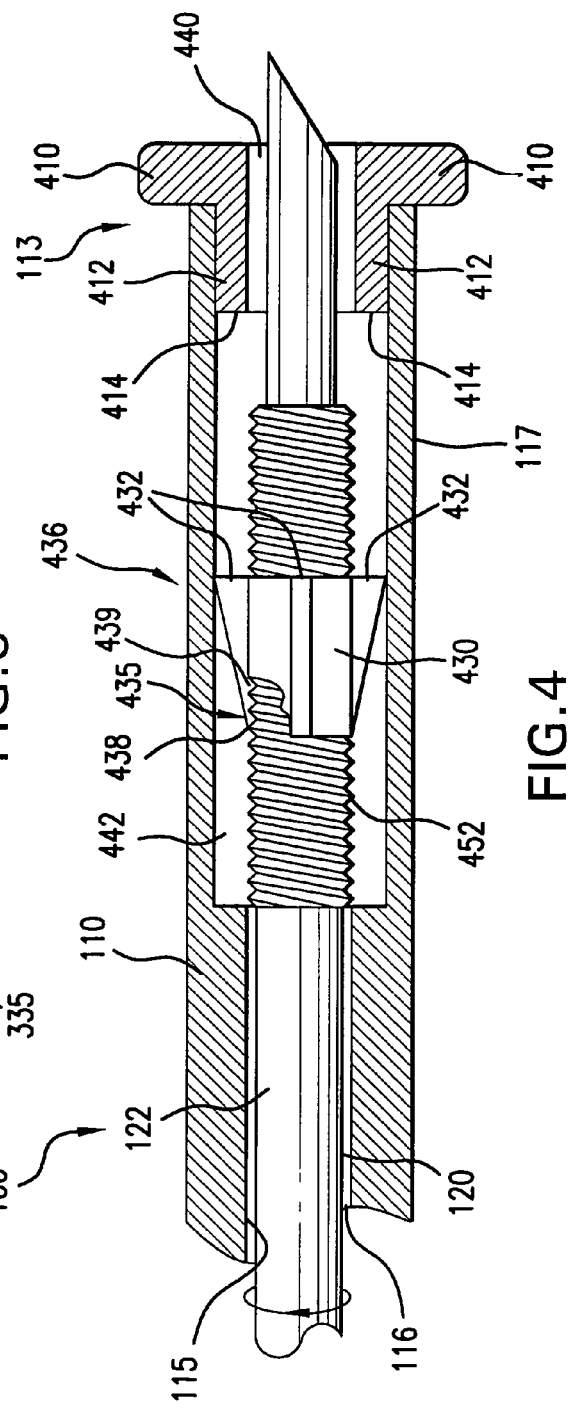

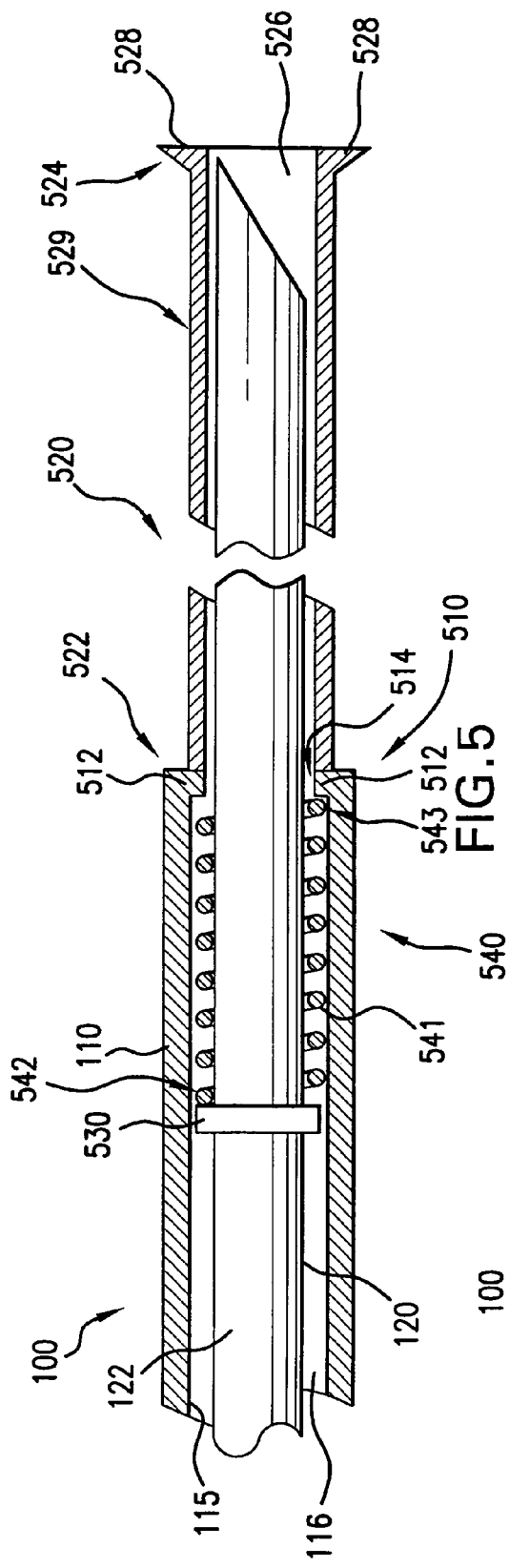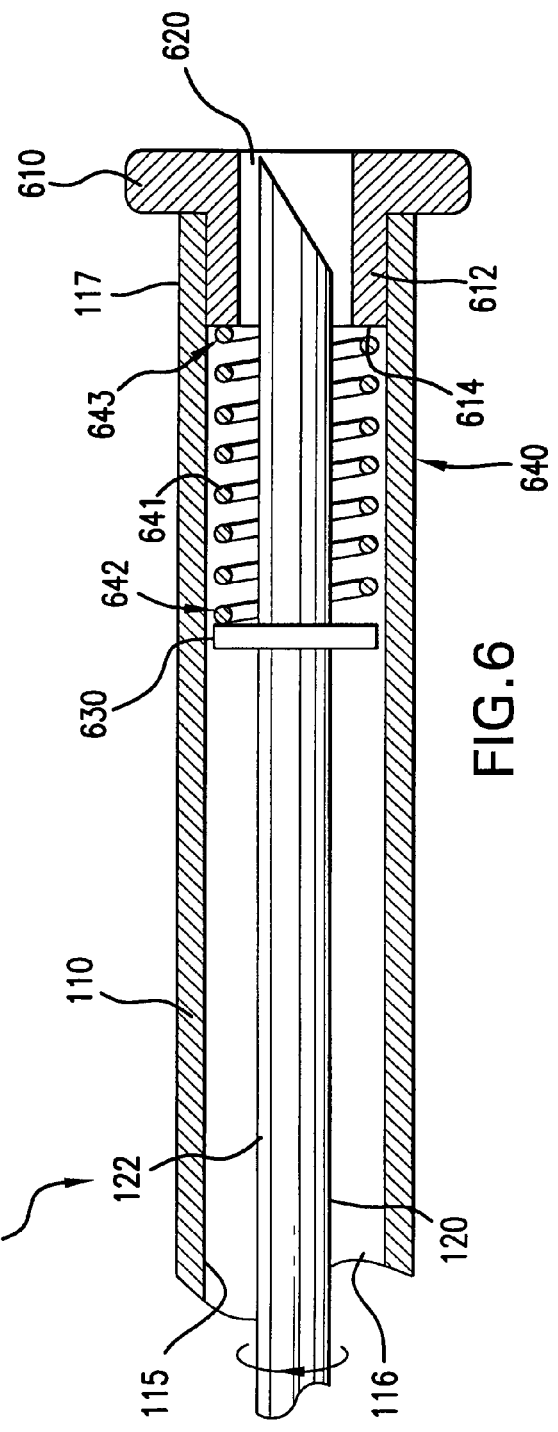

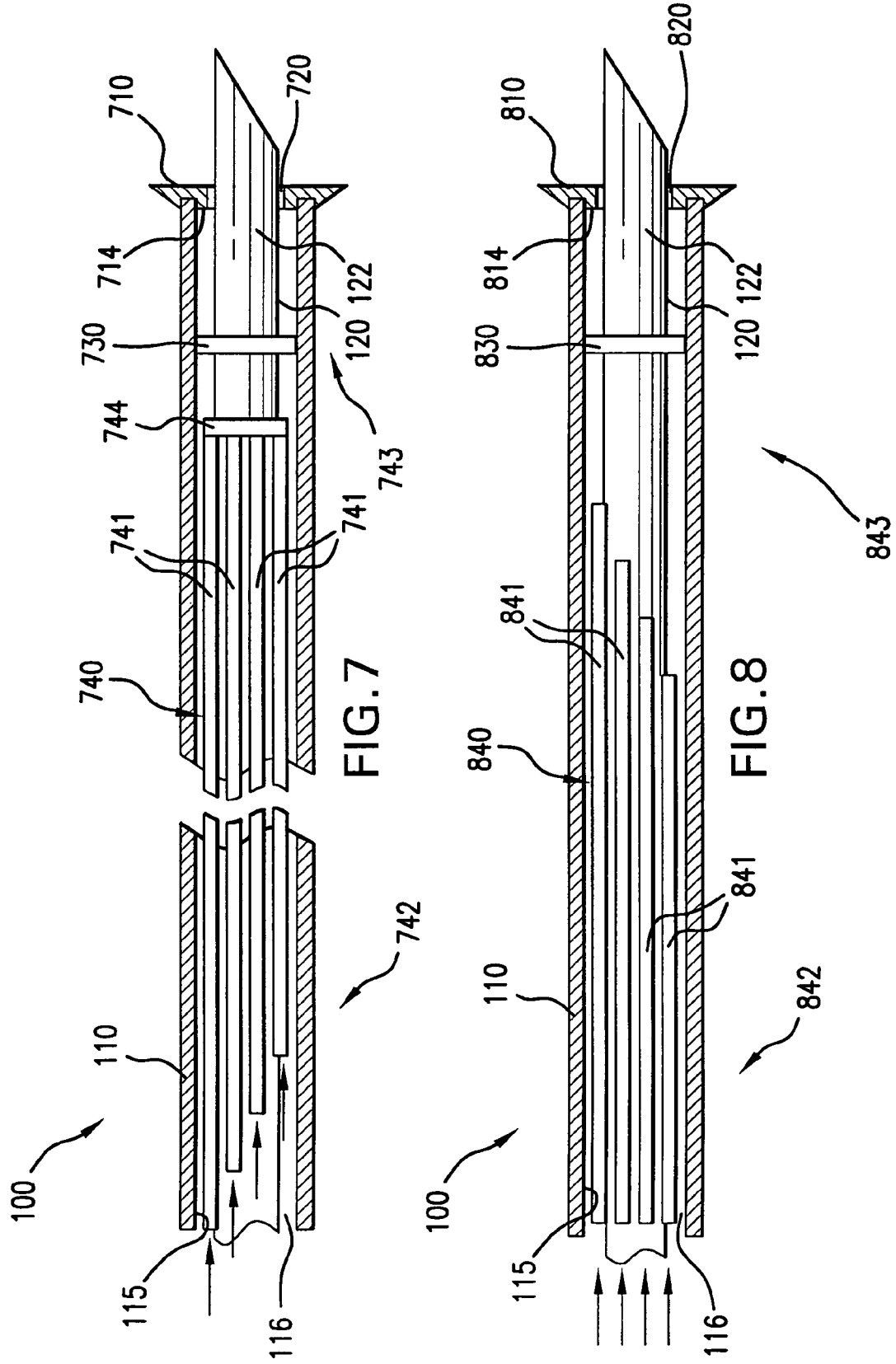

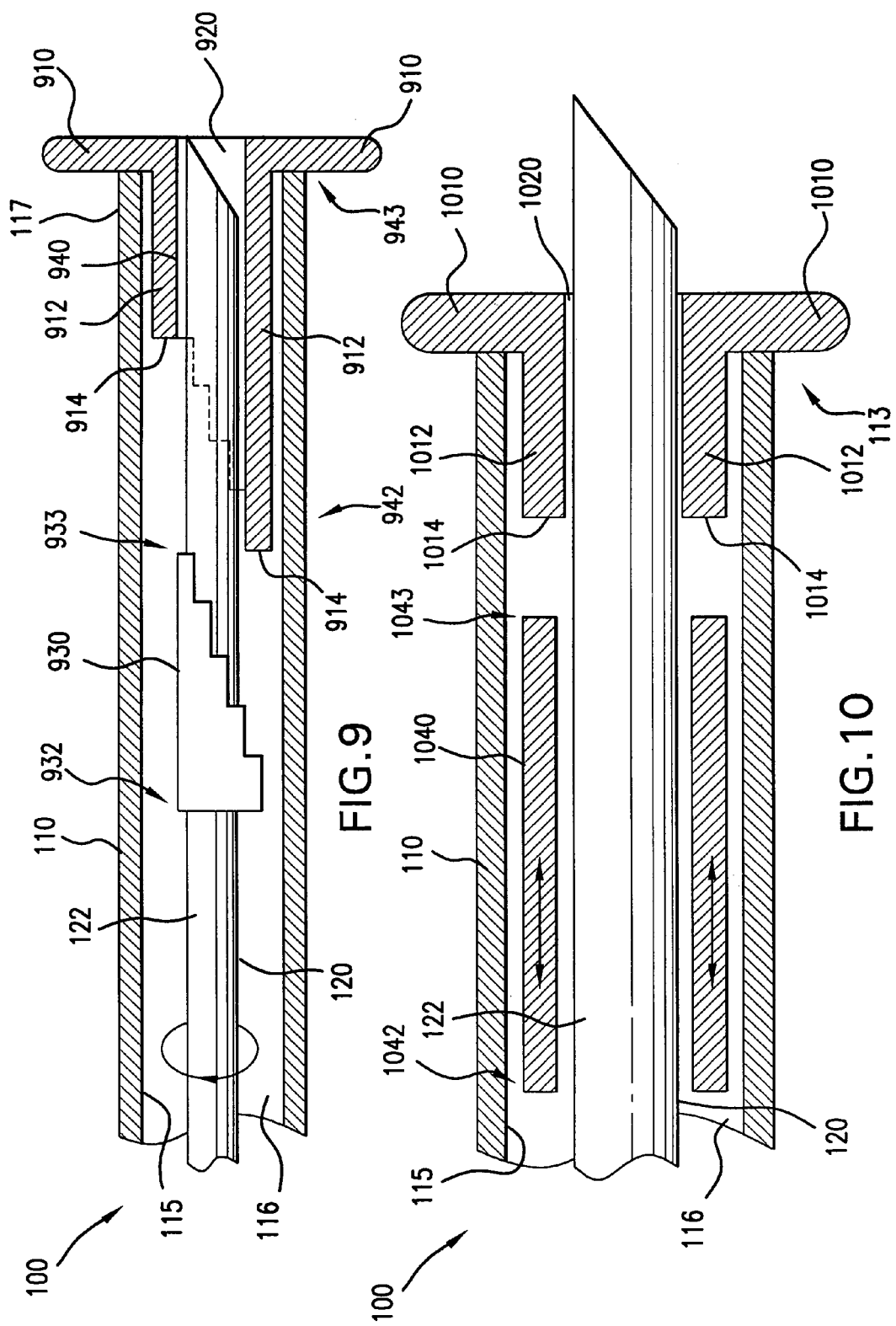

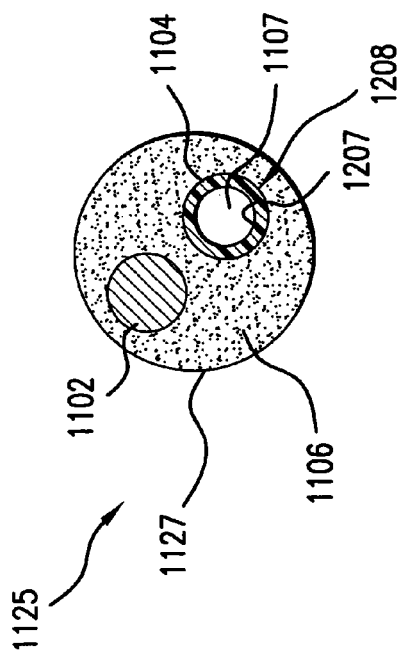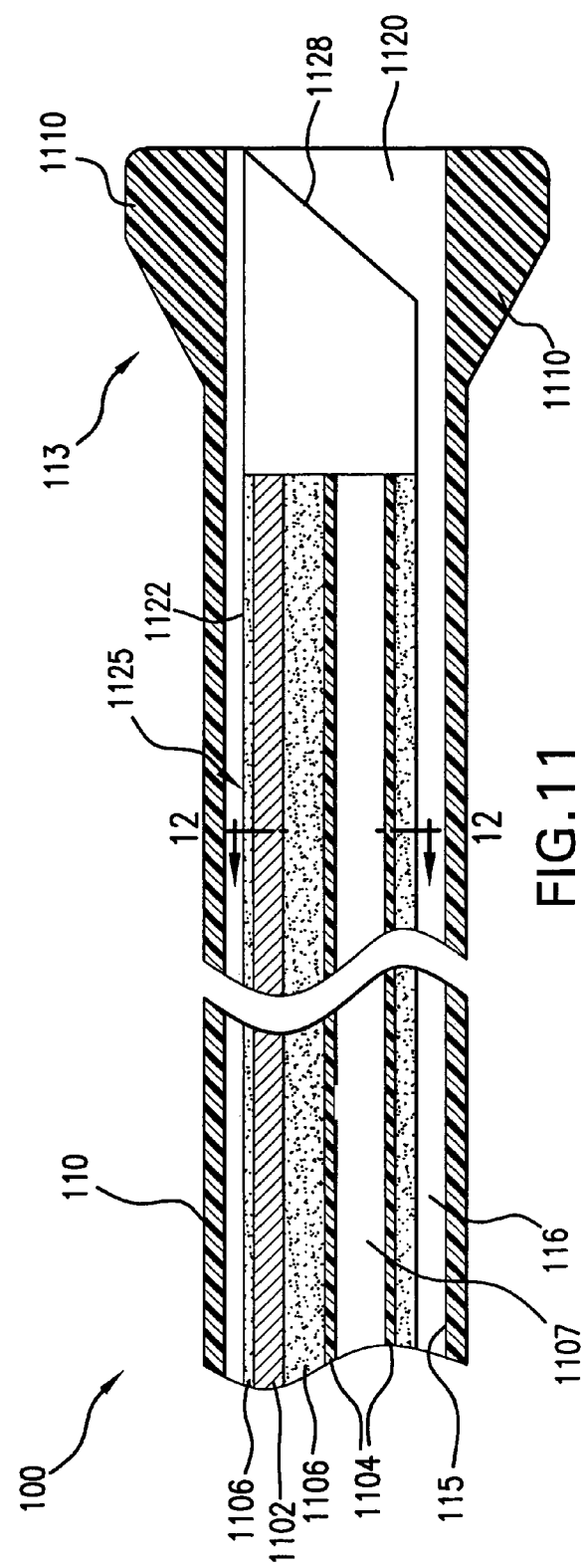

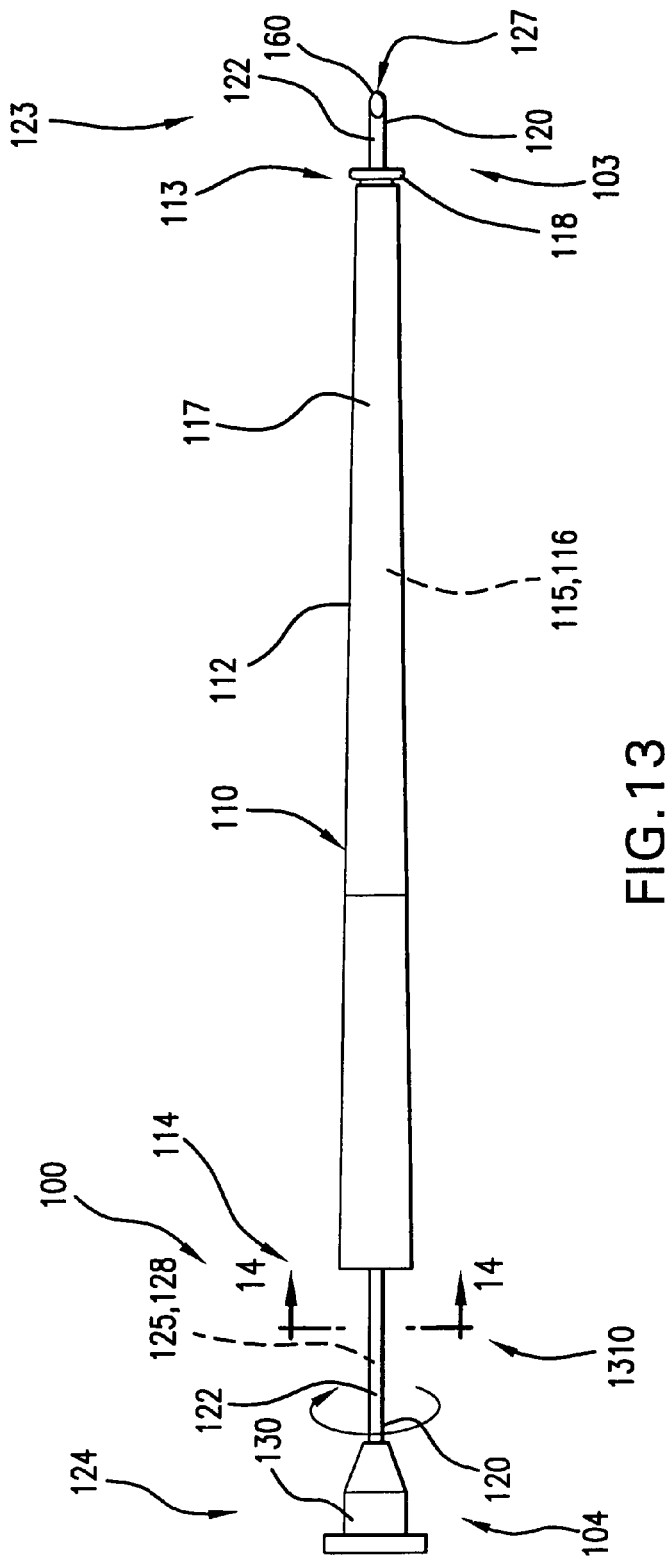

VARIABLE DEPTH INJECTION DEVICE AND METHOD

FIELD OF THE INVENTION

Embodiments of the present invention relate to injection catheters and methods for the injection of therapeutic and other agents at a target site within a patient's body. More particularly, the embodiments relate to variable depth injection catheter systems.

BACKGROUND

Medical catheters are used for innumerable minimally invasive medical procedures. Catheters may be used, for example, for delivery of therapeutic drug doses to target tissue and/or for delivery of medical devices such as lumen-reinforcing or drug-eluting stents. Likewise, catheters may be used to guide medical instruments to a target site to perform a surgical procedure, such as tissue rescission, ablation of obstructive deposits or myocardial revascularization.

Currently, myocardial injection devices are used to deliver therapeutics, for example, cell and viral therapeutics, to the myocardial wall to stimulate myocardial angiogenesis and myocardial tissue regeneration. Unfortunately, not all patients have ventricular walls of equal thickness, which makes it difficult to treat those patients with thin ventricular walls with a needle having a single depth. For example, if the depth of injection of the needle causes the needle tip to extend through the ventricular wall, the therapeutic will not be delivered to the desired location, and thus the effectiveness of the procedure will be compromised. Similarly, there is a wide range of wall thicknesses even within a single patient's heart, which requires multiple needles, each with a different depth of injection. As a result, procedural times and costs are increased due to using and switching between multiple needles.

Compounding the difficulty of using the correct depth of injection is the loss/gain in needle length due to the bending and curving of the catheter to reach the desired tissue site. For example, when a catheter lumen is inserted into and moved through a body, a needle lumen that is disposed within the catheter lumen will be subjected to similar movements and bends. However, for a variety of reasons, for example, friction between the inner and outer lumens, the amount of space between the inner and outer lumens, and different levels of lumen flexibility, the distal end of the inner lumen may not remain in the same relative position to the distal end of the outer lumen when the catheter is in a curved position as when it is in a straight position. In the case where the inner lumen is not as flexible as the outer lumen and the outer lumen has been contorted to have numerous curves, the inner lumen may extend past the end of outer lumen because it has taken a "path of least resistance" to short-cut through the curves in the outer lumen. As a result, the tip of the needle may extend out of the distal end of the catheter, thus making it difficult to move the end of the catheter without damaging tissue. In addition, having the tip of the needle extend out of the distal end of the catheter may change the depth of the injection to be too deep. Conversely, if friction prevents the inner lumen from moving the same amount as the outer lumen, the tip of the needle may not extend to its normal position within the outer lumen at the distal end of the catheter, thus reducing the depth of or even preventing the injection all together. For example, if the depth of injection is to be 2 mm and the inner needle lumen has receded 1.5 mm from its at rest position near the distal end of the catheter, then the actual depth of the injection will only be 0.5 mm.

SUMMARY OF THE INVENTION

The invention is directed to improved catheter systems with variable injection depths and related methods. In certain embodiments, a device and method are provided for injecting therapeutic and other agents or fluids at a target site within a patient's body. The device may include a catheter with a distal end and a proximal end and at least one catheter lumen extending therebetween. The device may also include a needle with a proximal end and a distal end with a needle lumen extending therebetween, the needle extending from a proximal end of the catheter to a distal end of the catheter and the needle to move in a one-to-one relationship with the catheter lumen to maintain a predetermined needle deployment length as the catheter lumen and needle are subjected to various bend configurations.

Other aspects of the invention are set forth in the appended claims.

BRIEF DESCRIPTION OF THE DRAWINGS

The foregoing and further features and advantages of the invention will become apparent from the following description of preferred embodiments with reference to the accompanying drawings, wherein like numerals are used to represent like elements and wherein:

FIG. 3 is a cross-sectional side view of a portion of the distal end of a catheter, in accordance with an embodiment of the present invention.

FIG. 4 is a partial cross-sectional side view of a portion of the distal end of a catheter, in accordance with an embodiment of the present invention.

FIG. 5 is a cross-sectional side view of a portion of the distal end of a catheter and is similar to FIG. 3, in accordance with an embodiment of the present invention.

FIG. 6 is a cross-sectional side view of a portion of the distal end of a catheter and is similar to FIG. 4, in accordance with an embodiment of the present invention.

FIG. 7 is a cross-sectional side view of a portion of the distal end of a catheter and is similar to FIG. 6, in accordance with an embodiment of the present invention.

FIG. 8 is a cross-sectional side view of a portion of the distal end of a catheter and is similar to FIG. 6, in accordance with an embodiment of the present invention.

FIG. 9 is a cross-sectional side view of a portion of the distal end of a catheter and is similar to FIG. 6, in accordance with an embodiment of the present invention.

FIG. 10 is a cross-sectional side view of a portion of the distal end of a catheter and is similar to FIG. 6, in accordance with an embodiment of the present invention.

FIG. 11 is a cross-sectional side view of a portion of the distal end of a catheter and is similar to FIG. 7, in accordance with an embodiment of the present invention.

FIG. 12 is a cross-sectional view of the needle of FIG. 1, in accordance with an embodiment of the present invention.

FIG. 13 is a plan view of a catheter including distal end, proximal end, and shaft assembly, in accordance with an embodiment of the present invention.

FIG. 14 is a cross-sectional view of the catheter of FIG. 13, in accordance with an embodiment of the present invention.

DETAILED DESCRIPTION

Figure 1:
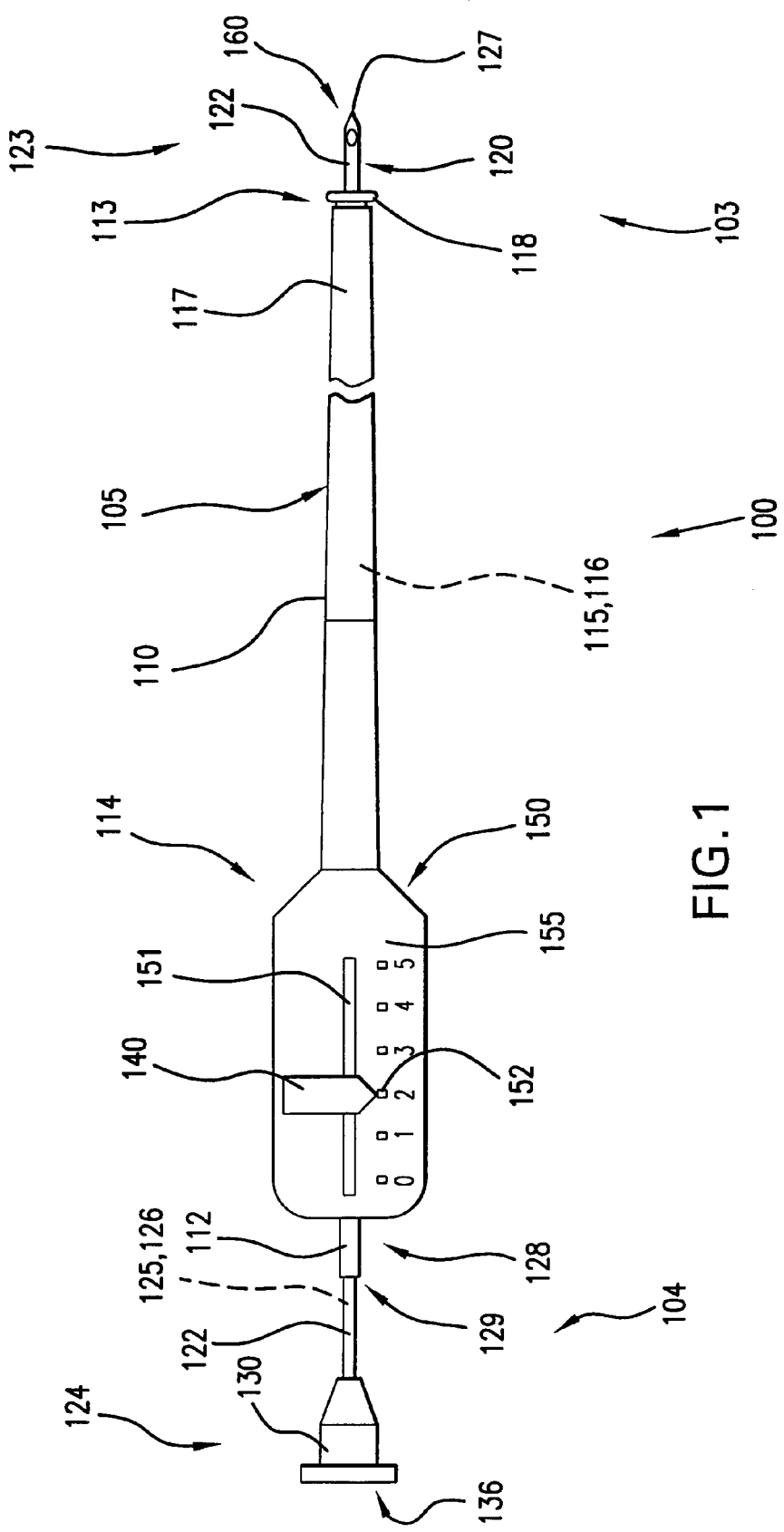
FIG. 1 is a plan view of a catheter including a distal end, a proximal end, and a shaft assembly, in accordance with an embodiment of the present invention.

Some embodiments of the present invention may include a needle-based direct injection device similar to, for example, a Stiletto catheter manufactured by Boston Scientific of Natick, Mass. For example, embodiments of the present invention may include catheters both with and without hoods. Likewise, embodiments of the present invention may include catheters with and without an electrode sensor tip. Similarly, some embodiments may include combinations of the above-described features in catheters with and without deflectable tips.

A more detailed description of the operation of a deflectable tip catheter and a control assembly may be found in U.S. Pat. No. 6,083,222, issued on Jul. 4, 2000 and entitled "Deflectable Catheter for Ablating Cardiac Tissue," which is hereby incorporated by reference in its entirety.

In accordance with an embodiment of the present invention, a variable needle length catheter may include an inner lumen disposed in an outer housing lumen. The catheter may permit adjustment of a needle injection depth while it is positioned inside a patient's body, which may reduce procedural time and costs due to the range in depth of injections available with the present invention. The inner lumen may be used to deliver a therapeutic agent directly through it to a target tissue area, for example, heart tissue, and to transmit force to a needle to inject the therapeutic into the target tissue. The inner lumen may also be able to withstand the longitudinal and latitudinal compressive forces acting on it to allow a consistent one-to-one movement from a proximal end to a distal end relative to the outer lumen. This one-to-one movement remains consistent regardless of the bending of the catheter. The outer lumen may be of sufficient rigidity to maintain an enlarged distal tip of the catheter against the target tissue without altering the one-to-one movement interactions between it and the inner lumen and without perforating the target tissue. The outer lumen and the inner lumen may together relative to each other with very little resistance.

In accordance with an embodiment of the present invention, the inner and outer lumens may be assembled, one over the other, with a minimum of space between the two lumens to allow for the one-to-one movement from the proximal end to the distal end. In addition to minimizing the spacing, the amount of friction between the two lumens may be significantly reduced by the use of a low-friction lining, for example, polytetrafluoroethylene. As a result, the two lumens will not change in relative length to one another when subjected to various bends such as seen in human vasculature. The inner lumen and the outer lumen may withstand known forces acting upon them such as column and frictional forces. The two lumens may also resist expansion and contraction due to temperature and moisture absorption and/or incorporate known temperature and absorptive material characteristics into the design to maintain the one-to-one movement of the two lumens regardless of the temperature or level of moisture.

FIG. 1 is a plan view of a catheter 100 including a distal end 103, a proximal end 104, and a shaft assembly 105, in accordance with an embodiment of the present invention. Shaft assembly 105 may comprise a first elongate shaft 110 having a distal end 113, a proximal end 114, and an inner surface 115 defining a lumen 116. Shaft assembly 105 may also include a second elongate shaft 112 defining a lumen slidingly disposed within lumen 116 of first elongate shaft 110. First elongate shaft 110 may also include an outer surface 117 extending between proximal end 114 and distal end 113 of first elongate shaft 110. First elongate shaft 110 may have a hood 118 attached at distal end 113 thereof. Hood 118 may define an opening in common with lumen 116 through which a third elongate shaft 120 may extend past distal end 113 of first elongate shaft 110. Third elongate shaft 120 may be slidingly disposed within a lumen defined by second elongate shaft 112.

In FIG. 1, third elongate shaft 120 may have an outer surface 122, a distal end 123, a proximal end 124, and an inner surface 125. Distal end 123 of third elongate shaft 120 may form a tip 127 having an injection port 160 that may be in fluid communication with proximal end 124 of third elongate shaft 120 through a lumen 126 defined by inner surface 125 of third elongate shaft 120. A hub 130 may be disposed about third elongate shaft 120 proximate proximal end 124 thereof. Hub 130 may define a proximal port 136, which may be in fluid communication with injection port 160 via injection lumen 128.

In many applications it may be desirable to advance distal end 123 of third elongate shaft 120 in FIG. 1 by a known distance relative to distal end 113 of first elongate shaft 110. In the embodiment of FIG. 1, a slider 140 may be fixed to second elongate shaft 112 proximate a proximal end 128 thereof, which may extend past proximal end 114 of first elongate shaft 110 and terminate with a proximal end 129. A portion of slider 140 may be disposed within a cavity 151 defined by a housing 150. In the present embodiment, housing 150 may be fixed to first elongate shaft 110 proximate proximal end 114 thereof and a plurality of indicia 152 may be disposed on a face 155 of housing 150 proximate slider 140. Indicia 152 may indicate a desired injection depth for third elongate shaft 120 measured, generally, in millimeters. Although, in FIG. 1, indicia 152 may only illustrate a scale of from 1 to 5 millimeters, contemplated injection depths may range from less than 1 millimeter to 10 or more millimeters, depending on the thickness of the tissue in which the injection is being directed.

A physician using catheter 100 in a surgical procedure may move distal end 123 of third elongate shaft 120 a known distance relative to distal end 113 of first elongate shaft 110 to set the desired injection depth. For example, a physician may urge slider 140 distally while visually observing the travel of slider 140 relative to indicia 152 of housing 150. The movement of slider 140 is translated via third elongate shaft 120 to distal end 123 of third elongate shaft 120. In accordance with an embodiment of the present invention, in FIG. 1, there may be substantially a one-to-one relationship between the movement of slider 140 relative to indicia 152 of housing 150 and the movement of distal end 123 of third elongate shaft 120 relative to distal end 113 of first elongate shaft 110.

Catheter 100, in FIG. 1, may be generally referred to as an injection catheter. It is to be appreciated that a catheter in accordance with the present invention may be any number of various types of catheters without deviating from the spirit and scope of the present invention.

In FIG. 1, in accordance with embodiments of the present invention, first elongate shaft 110 of catheter 100 may be an elongate tubular member having a reinforcement member, for example, a co-braided polymer tube, a co-extruded tube with two or more polymers, one or more rigid polymer or metallic wires or rods embedded in a polymer tube and two coaxial tubes, one being of a rigid nature mechanically joined by, for example, a heat shrink tube over a polymer tube.

In FIG. 1, in accordance with embodiments of the present invention, second elongate shaft 112 and third elongate shaft 120 may be made of various metallic and non-metallic hypodermic tubing materials. For example, metallic hypodermic tubing materials may include, but are not limited to, stainless steel and nickel-titanium alloy. Likewise, examples of non-metallic hypodermic tubing materials may include, but are not limited to, polycarbonate, poly(L-lactide) (PLLA), poly (D, L-lactide) (PLA), polyglycolide (PGA), poly(L-lactide-co-D, L-(lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyhydroxybutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phosphate ester) poly(amino acid), poly(hydroxy butyrate), polyacrylate, polyacrylamide, poly(hydroxyethyl methacrylate), polyurethane, polysiloxane and their copolymers, polyethylene (PE), polypropylene (PP), polyvinylchloride (PVC), polytetrafluoroethylene (PTFE), polyether block amide (PEBA), polyamide and polyimide.

In FIG. 1, in accordance with embodiments of the present invention, regardless of which materials are used for first elongate shaft 110, second elongate shaft 112, and third elongate shaft 120, inner surface 115 of first elongate shaft 110 and an outer surface of second elongate shaft 112 move in a one-to-one relationship as catheter 100 is subjected to the bending and curving movements experienced by catheter 100 during use. Similarly, third elongate shaft 120 and second elongate shaft 112 move in a one-to-one relationship as second elongate shaft 112 is subjected to the bending and curving movements experienced by catheter 100 during use.

Figure 2:
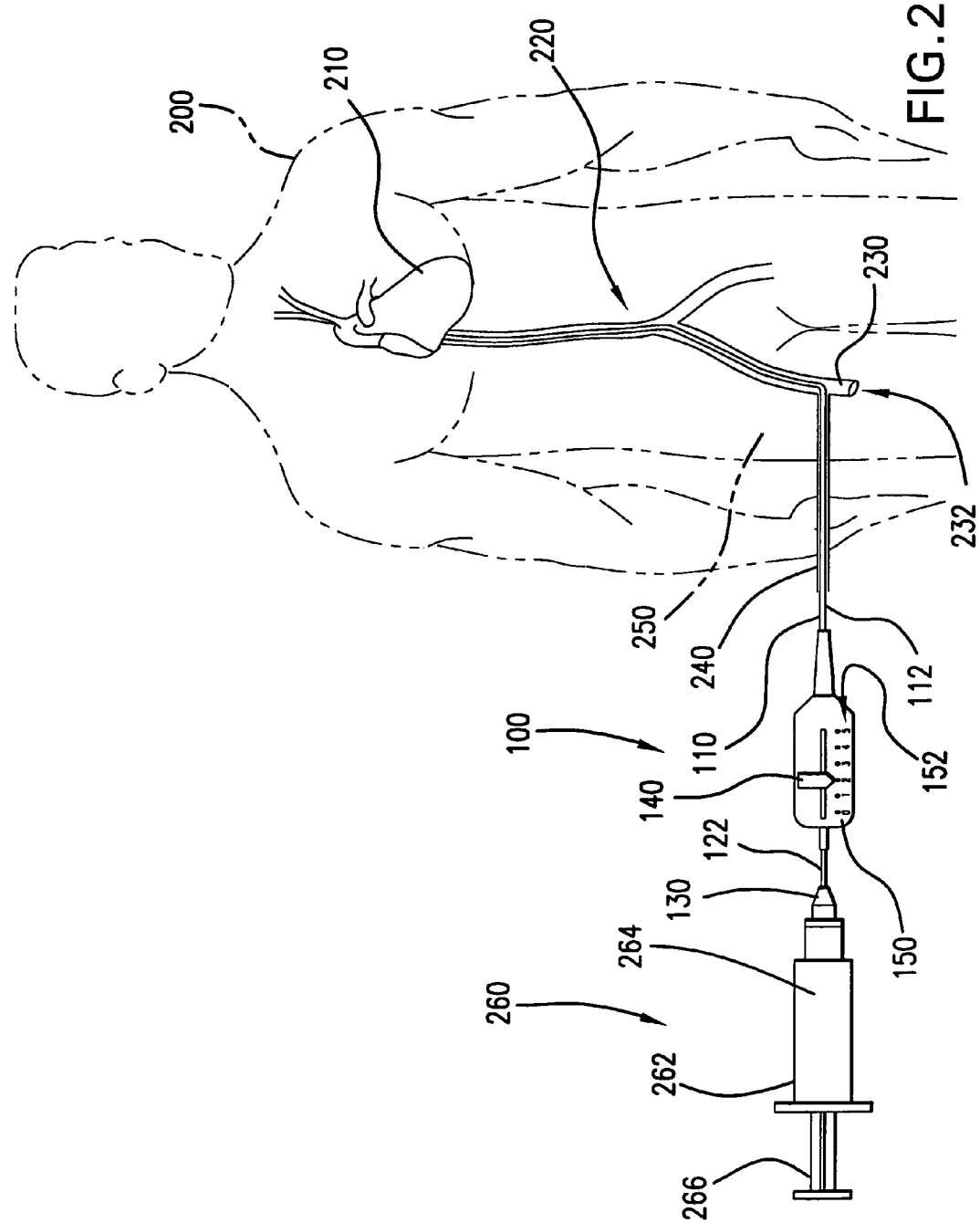
FIG. 2 is a diagrammatic view including a catheter and a patient with a heart and a vascular system including a blood vessel defining a blood vessel lumen, in accordance with an embodiment of the present invention.

FIG. 2 is a diagrammatic view including catheter 100 and a patient 200 with a heart 210 and a vascular system 220 including a blood vessel 230 defining a blood vessel lumen 232, in accordance with an embodiment of the present invention. An access sheath 240 is partially disposed within a leg 250 of patient 200. A distal end of access sheath 240 may be disposed within blood vessel lumen 232 of blood vessel 230. Access sheath 240 may aid in the introduction of catheter 100 into blood vessel lumen 232.

In FIG. 2, in accordance with an embodiment of the present invention, a portion of catheter 100 may be disposed within blood vessel lumen 232 of blood vessel 230 so that distal end 103 (not visible) of catheter 100 may be disposed within heart 210. Specifically, distal end 103 of catheter 100 may be disposed against tissue, for example, a wall of heart 210. Third elongate shaft 120 may be extended past distal end 113 of first elongate shaft 110 and into the tissue against which distal end 103 of catheter 100 is disposed, to deliver a therapeutic to the tissue in contact with distal end 103 of catheter 100.

In FIG. 2, in accordance with an embodiment of the present invention, catheter 100 may be generally referred to as an injection catheter, which may include various types of catheters without departing from the spirit and scope of the present invention. For example, catheter 100 may be, but is not limited to, a hooded injection catheter, an un-hooded injection catheter, and/or a deflectable-tip injection catheter.

In FIG. 2, in accordance with some embodiments of the present invention, a fluid source 260 may be coupled to hub 130 to supply fluid to needle lumen 128. In FIG. 2, fluid source 260 may include a variable volume chamber 262 defined by a body 264 in which a plunger 266 may be slidingly disposed. Variable volume chamber 262 may be in fluid communication with injection lumen 128 of third elongate shaft 120. Urging plunger 266 distally may have the effect of urging fluid into injection lumen 128 of third elongate shaft 120. A number of energy sources may be used to urge plunger 266 distally, for example, but not limited to, springs, compressed gas, a human being, and electricity. Various additional embodiments of fluid source 260 are possible without deviating from the spirit and scope of the present invention. Examples of fluid sources which may be suitable in some applications include syringes, peristaltic pumps, and an I.V. bag with pressure applied to an outer surface thereof.

A more detailed description of catheter 100 and methods of its use may be found in related U.S. patent application Ser. No. 09/635,083, entitled, "Catheter Shaft Assembly," which is hereby incorporated herein in its entirety, as well as in PCT publication WO 02/11808, published Feb. 12, 2002, which claims priority to U.S. patent application Ser. No. 09/635, 083.

FIG. 3 is a cross-sectional side view of a portion of the distal end of catheter 100, in accordance with an embodiment of the present invention. In FIG. 3, first elongate shaft 110 of catheter 100 may include an inwardly flanged distal end 310, having a flange 312 defining an opening 314, to which a flared tip section 320 is co-axially aligned and attached. Flared tip section 320 has a proximal end 322 attached to a distal side of flange 312, a distal end 324, a flared tip lumen 326 therebetween, and a flared tip 328 at distal end 324. Flared tip lumen 326 is in communication with catheter lumen 116, and third elongate shaft 120 (hereinafter interchangeably referred to as needle 120) may be disposed through catheter lumen 116 and opening 314 in flange 312 into and through flared tip lumen 326. In an embodiment of the present invention, flared tip section 320 may have a length up to about 10 inches or more. Needle 120 may be extended past distal end 324 of flared tip section 320. Flared tip section 320 may be of variable length depending on the desired characteristics and functioning of flared tip section 320. For example, in another embodiment, flared tip section 320 may extend up to 15 inches or more in length. Flared tip 328 may form a circumferential ring around an outer surface 329 of flared tip section 320 at distal end 324 of flared tip section 320. Flared tip 328 may be of sufficient width to prevent flared tip 328 from perforating tissue with which it comes in contact. In embodiments of the present invention, flared tip 328 may be formed as an integral part of flared tip section 320 or it may be an attached component.

In FIG. 3, in accordance with an embodiment of the present invention, outer surface 122 of needle 120 may be surrounded by and engaged with a needle depth control device 330, in the form of a stop collar, located proximate a proximal side of flange 312 of first elongate shaft 110. Needle depth control device 330 may include a plurality of longitudinal protrusions 332, for example, rails, with an inner surface 338 with a first thread 339 disposed thereon, a proximal end 335 and a distal end 336. Longitudinal protrusions 332 may be slidingly disposed in an equal plurality of longitudinal grooves 342 disposed in inner surface 115 of first elongate shaft 110 to permit movement along the longitudinal axis of catheter 100. Similarly, longitudinal grooves 342 prevent lateral movement of longitudinal protrusions 332. Longitudinal grooves 342 may extend for several inches from the proximal side of flange 312 toward proximal end 104 of catheter 100. A section of outer surface 122 of needle 120 may contain a second thread 352 that is the reciprocal of and may engage first thread 339 upon movement of needle 120 toward the distal end of catheter 100. Although in the embodiment shown in FIG. 3 second thread 352 on needle 120 is shown to extend approximately the length of needle depth control device 330, other embodiments are possible in which second thread 352 may extend for longer and/or shorter distances. The extent of the engagement of first thread 339 and second thread 352 may be controlled from proximal end 124 of needle 120 by turning needle 120 to engage and/or disengage needle 120 with needle depth control device 330. Distal end 336 of needle depth control device 330 may function as a stop collar when it contacts the proximal side of flange 312 of first elongate shaft 110 upon needle 120 being urged toward distal end 103 of catheter 100. Therefore, an injection depth, that is, the distance needle 120 may be extended past distal end 324 of flared tip section 320, may be limited by setting needle depth control device 330 to a predetermined distance. For example, to set the injection depth to 5 mm past flared tip 328, needle depth controller 330 is set to travel only 5 mm before contacting the proximal side of flange 312. Although the predetermined distance may be selected at the proximal end of catheter 100, the distance is controlled at the distal end of catheter 100 by the needle depth control device 330.

FIG. 4 is a partial cross-sectional side view of a portion of the distal end of catheter 100, in accordance with another embodiment of the present invention. In FIG. 4, first elongate shaft 110 of catheter 100 may include a generally circular hood 410 having a proximally extending circular wall 412 (hood 410 shown as having a generally L-shaped cross-section in the embodiment in FIG. 4) attached at the distal end of catheter 100. In FIG. 4, hood 410 may also be attached to inner surface 115 of first elongate shaft 110 to form a stop mechanism 414 with the proximal end of proximally extending circular wall 412. In FIG. 4, hood 410 may define an opening 440 co-axially aligned with catheter lumen 116 and of sufficient size to permit needle 120 to pass therethrough.

In accordance with other embodiments of the present invention, in FIG. 4, hood 410 may include a generally circular hood similar to circular hood 410 having a similar proximally extending circular wall so as to have a generally T-shaped cross-section. An interior surface of the proximally extending circular wall may be of sufficient size to fit around and attach to outer surface 117 at the distal end of first elongate shaft 110. The hood in this embodiment may also define an opening co-axially aligned with and smaller than catheter lumen 116, but of sufficient size to permit needle 120 to pass therethrough. Alternatively, an exterior surface of proximally extending circular wall of circular hood having the T-shaped cross-section embodiment may be attached to inner surface 115 at the distal end of first elongate shaft 110. The hood in this embodiment may also define an opening as in the other embodiments.

In FIG. 4, in accordance with an embodiment of the present invention, outer surface 122 of needle 120 may be surrounded by and engaged with a needle depth control device 430 in the form of a stop collar located proximate proximal side of stop mechanism 414. Needle depth control device 430 may include a plurality of longitudinal protrusions 432, for example, rails, a proximal end 435 and a distal end 436. In FIG. 4, needle depth control device 430 may include four, for example, wedge-shaped, longitudinal protrusions 432, which increase in height from proximal end 435 to distal end 436 of needle depth control device 430. The distal ends of each longitudinal protrusion 432 may form a stop collar to contact stop mechanism 414 of hood 410. Longitudinal protrusions 432 may be slidingly disposed in an equal plurality of longitudinal grooves 442 disposed in inner surface 115 of catheter 100 to permit movement along the longitudinal axis of catheter 100. Similarly, plurality of longitudinal grooves 442 may prevent lateral movement of longitudinal protrusions 432. The taper of wedge-shaped, longitudinal protrusions 432 help reduce friction as longitudinal protrusions 432 move in longitudinal grooves 442.

In FIG. 4, longitudinal grooves 442 may extend proximally for several inches from distal end 113 of first elongate shaft 110 toward proximal end 104 of catheter 100. Needle depth control device 430 may include an inner surface 438 with a first thread 439 disposed thereon. A section of outer surface 122 of needle 120 may contain a second thread 452 that is the reciprocal of and may selectively engage first thread 439 upon movement of needle 120 toward the distal end of catheter 100. It will be appreciated that the threads 452 may be continuous, although only a portion of the threads are shown in the partial cut-away view through needle depth control device 430. Although in the embodiment shown in FIG. 4 second thread 452 on needle 120 is shown to extend beyond the length of needle depth control device 430, other embodiments are possible in which second thread 452 may extend for longer and/or shorter distances. The extent of the engagement of first thread 439 and second thread 452 may be controlled from proximal end 124 of needle 120 by turning needle 120 to engage needle 120 with needle depth control device 430 in both the distal and proximal directions. Distal end 436 of needle depth control device 430 may function as a stop collar when it contacts the stop mechanism 414 upon needle 120 being urged toward distal end 103 of catheter 100. Therefore, the injection depth may be limited by setting needle depth control device 430 to a predetermined distance. Although the predetermined distance may be selected at the proximal end of catheter 100, the distance is controlled at the distal end of catheter 100 by the needle depth control device 430. Unlike FIG. 3, in FIG. 4, needle depth control device 430 may be located nearer to distal end 123 of needle 120, for example, within about 1-3", than in FIG. 3, which may be 10-15" or more away from the distal end of the needle.

FIG. 5 is a cross-sectional side view of a portion of the distal end of catheter 100 and is similar to the distal end of first elongate shaft 110 of FIG. 3, in accordance with an embodiment of the present invention. In FIG. 5, first elongate shaft 110 of catheter 100 may include an inwardly flanged distal end 510, having a flange 512 defining an opening 514, to which a flared tip section 520 is co-axially aligned and attached. Flared tip section 520 has a proximal end 522 attached to a distal side of flange 512, a distal end 524, a flared tip lumen 526 therebetween, and a flared tip 528 at distal end 524. Flared tip lumen 526 is in communication with catheter lumen 116, and needle 120 may be disposed through catheter lumen 116 and opening 514 in flange 512 into and through flared tip lumen 526. Needle 120 may be extended past distal end 524 of flared tip section 520. Flared tip section 520 may be of variable length depending on the desired characteristics and functioning of flared tip section 520. For example, flared tip section 520 may extend up to 15 inches or more in length. Flared tip 528 may form a circumferential ring around an outer surface 529 of flared tip section 520 at distal end 524 of flared tip section 520. Flared tip 528 may be of sufficient width to prevent flared tip 528 from perforating tissue with which it comes in contact. In embodiments of the present invention, flared tip 528 may be formed as an integral part of flared tip section 520 or it may be an attached component.

In FIG. 5, in accordance with an embodiment of the present invention, outer surface 122 of needle 120 may be coaxially aligned with and attached to a stop collar 530. Needle 120 may also be co-axially aligned with and surrounded by a needle depth control device 540 located proximate a proximal side of flange 512 of first elongate shaft 110 and distal a distal side of stop collar 530. Needle depth control device 540 may include an interstitial member 541 such as a coil and/or a spring. Interstitial member 541 may include a proximal end 542 and a distal end 543 and may be in an uncompressed condition when not engaged between the distal side of stop collar 530 and proximal side of flange 512. Interstitial member 541 may also have a known spring constant, which affects the amount of force that needs to be applied to compress the spring. However, having a known spring constant enables the specific amounts of force needed to compress interstitial member 541 a given set of distances to be calculated. Interstitial member 541 may bias stop collar 530 away from flange 512 when interstitial member 541 is compressed by stop collar 530. Distal end 543 of interstitial member 541 may contact and stop against the proximal side of flange 512 of first elongate shaft 110 upon needle 120 being urged toward distal end 103 of catheter 100. Therefore, an injection depth, that is, the distance needle 120 may be extended past distal end 524 of flared tip section 520, may be specified by selecting one of the calculated amounts of force needed to compress the interstitial member 541 the desired distance. However, for ease of use, the conversion between force and distance may be already reflected at the proximal end of catheter 100 so that setting the injection depth may be accomplished by selecting the desired depth. To set the depth to 5 mm past flared tip 328, as limited by interstitial member 541, the depth may be selected using, for example, but not limited to, a sliding scale, push button selector, and/or dialing mechanism. As in the previously described embodiments, in the present embodiment, although the predetermined distance may be selected at the proximal end of catheter 100, control of the distance occurs near the distal end of catheter 100.

FIG. 6 is a cross-sectional side view of a portion of the distal end of catheter 100 and is similar to the distal end of first elongate shaft 110 of FIG. 4, in accordance with another embodiment of the present invention. In FIG. 6, first elongate shaft 110 of catheter 100 may include a generally circular hood 610 having a proximally extending circular wall 612 (hood 610 shown as having a generally L-shaped cross-section in the embodiment in FIG. 6) attached at the distal end of catheter 100. In FIG. 6, hood 610 may also be attached to inner surface 115 of first elongate shaft 110 to form a stop mechanism 614 with the proximal end of proximally extending circular wall 612. In FIG. 6, hood 610 may define an opening 620 co-axially aligned with catheter lumen 116 and of sufficient size to permit needle 120 to pass therethrough.

In accordance with other embodiments of the present invention, in FIG. 6, hood 610 may include a generally circular hood similar to circular hood 610 having a similar proximally extending circular wall so as to have a generally T-shaped cross-section. An interior surface of the proximally extending circular wall may be of sufficient size to fit around and attach to outer surface 117 at the distal end of first elongate shaft 110. The hood in this embodiment may also define an opening co-axially aligned with and smaller than catheter lumen 116, but of sufficient size to permit needle 120 to pass therethrough. Alternatively, an exterior surface of proximally extending circular wall of circular hood having the T-shaped cross-section embodiment may be attached to inner surface 115 at the distal end of first elongate shaft 110. The hood in this embodiment may also define an opening as in the other embodiments.

In FIG. 6, in accordance with an embodiment of the present invention, outer surface 122 of needle 120 may be coaxially aligned with and have a stop collar 630 attached near the distal end of needle 120 and on the proximal side of stop mechanism 614. Needle depth control device 640 may include an interstitial member 641 such as a coil and/or a spring. Interstitial member 641 may include a proximal end 642 and a distal end 643 and may be disposed between a distal side of stop collar 630 and the proximal side of stop mechanism 614. Interstitial member 641 may be in an uncompressed condition when not engaged between the distal side of stop collar 630 and the proximal side of stop mechanism 614. Interstitial member 641 may also have a known spring constant, which affects the amount of force that needs to be applied to compress the spring. However, having a known spring constant enables the specific amounts of force needed to compress interstitial member 641 a given set of distances to be calculated. Interstitial member 641 may bias stop collar 630 away from the stop mechanism 614 when interstitial member 641 is compressed by stop collar 630. Distal end 643 of interstitial member 641 may contact and stop against the proximal side of stop mechanism 614 upon needle 120 being urged toward distal end 103 of catheter 100. Therefore, an injection depth, that is, the distance needle 120 may be extended past the distal side of hood 610, may be specified by selecting one of the calculated amounts of force needed to compress the interstitial member 641 the desired distance. However, for ease of use, the conversion between force and distance may be already reflected at the proximal end of catheter 100 so that setting the injection depth may be accomplished by selecting the desired depth. To set the depth to 5 mm past hood 610, as limited by interstitial member 641, the depth may be selected using, for example, but not limited to, a sliding scale, push button selector, and/or dialing mechanism. As in the previously described embodiments, in the present embodiment, although the predetermined distance may be selected at the proximal end of catheter 100 control of the distance occurs near the distal end of catheter 100.

FIG. 7 is a cross-sectional side view of a portion of the distal end of catheter 100 and is similar to the distal end of first elongate shaft 110 of FIG. 6, in accordance with another embodiment of the present invention. In FIG. 7, first elongate shaft 110 of catheter 100 may include a flared tip 710 at the distal end of first elongate shaft 110. Flared tip 710 may form a circumferential ring around distal end 113 of first elongate shaft 110, and flared tip 710 may be of sufficient width to prevent flared tip 710 from perforating tissue with which it comes in contact. In embodiments of the present invention, flared tip 710 may be formed as an integral part of first elongate shaft 110, or it may be an attached component. Regardless, in FIG. 7, flared tip 710 may define an opening 720 co-axially aligned with and smaller than catheter lumen 116, but of sufficient size to permit needle 120 to pass therethrough. As such, flared tip 710 may extend over and partially close off catheter lumen 116, to act as a stop mechanism 714 to prevent needle 120 from extending beyond a selected depth.

In FIG. 7, in accordance with an embodiment of the present invention, outer surface 122 of needle 120 may be coaxially aligned with and have a stop collar 730 attached near the distal end of needle 120. In addition, outer surface 122 of needle 120 may be completely and/or partially surrounded by a needle depth control device 740 located proximate a proximal end of stop collar 730 near the distal end of needle 120. Needle depth control device 740 may include a plurality of interstitial members 741, for example, a plurality of longitudinal push rods, that may each include a proximal end 742 and a distal end 743. Each of the plurality of longitudinal push rods may have a different length and the distal ends of each of the plurality of longitudinal push rods may be attached to the proximal end of a push plate 744, which may be located proximate to the proximal end of stop collar 730. Each of the plurality of longitudinal push rods may possess sufficient stiffness to transmit a distally directed force to cause push plate 742 to move distally, contact the proximal side of stop collar 730, and extend needle 120 out past the distal side of flared tip 710. One or more pushing pins (not shown) may extend from the proximal end of catheter 100 to just proximate of the proximal end of the plurality of longitudinal push rods. In accordance with an embodiment of the present invention, a single pushing pin may be implemented that may be rotated around needle 120 in catheter lumen 116 to select which of the plurality of longitudinal push rods is to be contacted. In FIG. 7, proximal ends 742 of each of the plurality of longitudinal push rods extend different distances from push plate 744 to form a generally stair-step configuration. In embodiments of the present invention, the pushing pin may be extended a consistent predetermined distance so that needle movement is determined by which one of the plurality of longitudinal push rods the pushing pin engages.

In FIG. 7, the distal end of push plate 744 may contact the proximal side of stop collar 730 to urge needle 120 toward distal end 103 of catheter 100. Therefore, an injection depth, that is, the distance needle 120 may be extended past the distal side of flared tip 710, may be specified by selecting one of the predetermined injection depths associated with the plurality of longitudinal push rods. To set the depth past flared tip 710, as limited by interstitial member 741, the depth may be selected using, for example, but not limited to, a sliding scale, push button selector, and/or dialing mechanism. As in previously described embodiments, in the present embodiment, although the predetermined distance may be selected at the proximal end of catheter 100 control of the distance occurs near the distal end of catheter 100.

FIG. 8 is a cross-sectional side view of a portion of the distal end of catheter 100 and is similar to the distal end of first elongate shaft 110 of FIG. 6, in accordance with another embodiment of the present invention. In FIG. 8, first elongate shaft 110 of catheter 100 may include a flared tip 810 at the distal end of first elongate shaft 110. Flared tip 810 may form a circumferential ring around distal end 113 of first elongate shaft 110, and flared tip 810 may be of sufficient width to prevent flared tip 810 from perforating tissue with which it comes in contact. In an embodiment of the present invention, flared tip 810 may be formed as an integral part of first elongate shaft 110, or it may be an attached component. Regardless, in FIG. 8, flared tip 810 may define an opening 820 co-axially aligned with and smaller than catheter lumen 116, but of sufficient size to permit needle 120 to pass therethrough. As such, flared tip 810 extends over and partially closes off catheter lumen 116, to act as a stop mechanism 814 to prevent needle 120 from extending beyond a selected depth.

In FIG. 8, in accordance with an embodiment of the present invention, outer surface 122 of needle 120 may be coaxially aligned with and have a stop collar 830 attached near the distal end of needle 120. In addition, outer surface 122 of needle 120 may be completely and/or partially surrounded by a needle depth control device 840 located proximate the proximal end of stop collar 830 near the distal end of needle 120. Needle depth control device 840 may include a plurality of interstitial members 841, for example, a plurality of longitudinal push rods that may include a proximal end 842 and a distal end 843. Each of the plurality of longitudinal push rods may have a different length, and the distal ends of each of the plurality of longitudinal push rods may be at different distances away from the proximal side of stop collar 830. Each of the plurality of longitudinal push rods possesses sufficient stiffness to transmit a distally directed force, contact the proximal side of stop collar 830, and extend needle 120 out past the distal side of flared tip 810. One or more pushing pins (not shown) may extend from the proximal end of catheter 100 to just proximate of the proximal end of the plurality of longitudinal push rods. In accordance with an embodiment of the present invention, a single pushing pin may be implemented that may be rotated around needle 120 in catheter lumen 116 to select which of the plurality of longitudinal push rods is to be contacted. In FIG. 8, since the distal ends of each of the plurality of longitudinal push rods are located different distances from stop collar 830, they form a generally stair-step configuration. In embodiments of the present invention, the pushing pin may be extended a consistent predetermined distance so that needle movement is determined by which one of the plurality of longitudinal push rods the pushing pin engages.

In FIG. 8, the distal end of the selected longitudinal push rod may contact the proximal side of stop collar 830 to urge needle 120 toward distal end 103 of catheter 100. Therefore, an injection depth, that is, the distance needle 120 may be extended past the distal side of flared tip 810, may be specified by selecting one of the predetermined injection depths, which are associated with the plurality of longitudinal push rods. To set the depth past flared tip 810, as limited by interstitial member 841, the depth may be selected using, for example, but not limited to, a sliding scale, push button selector, and/or dialing mechanism. As in the previously described embodiments, in the present embodiment, although the predetermined distance may be selected at the proximal end of catheter 100, control of the distance occurs near the distal end of catheter 100.

FIG. 9 is a cross-sectional side view of a portion of the distal end of catheter 100 and is similar to the distal end of first elongate shaft 110 of FIG. 6, in accordance with another embodiment of the present invention. In FIG. 9, first elongate shaft 110 of catheter 100 may include a generally circular hood 910 having a proximally extending circular wall 912 (hood 910 shown as having a general L-shaped cross-section in the embodiment in FIG. 9) attached at the distal end of first elongate shaft 110. Hood 910 may form a circumferential ring around distal end 113 of first elongate shaft 110, and hood 910 may be of sufficient width to prevent hood 910 from perforating tissue with which it comes in contact. In FIG. 9, hood 910 may be attached to inner surface 115 of first elongate shaft 110 to form a stop mechanism 914 with the proximal end of proximally extending circular wall 912.

In other embodiments of the present invention, hood 910 may be formed as an integral part of first elongate shaft 110. Regardless, in FIG. 9, hood 910 may define an opening 920 co-axially aligned with and smaller than catheter lumen 116, but of sufficient size to permit needle 120 to pass therethrough. As such, hood 910 may extend over and partially close off catheter lumen 116, to act as stop mechanism 914 to prevent needle 120 from extending beyond a selected depth.

In accordance with other embodiments of the present invention, in FIG. 9, hood 910 may include a generally circular hood similar to circular hood 910 having a similar proximally extending circular wall so as to have a generally T-shaped cross-section. An interior surface of the proximally extending circular wall may be of sufficient size to fit around and attach to outer surface 117 at the distal end of first elongate shaft 110. The hood in this embodiment may also define an opening co-axially aligned with and smaller than catheter lumen 116, but of sufficient size to permit needle 120 to pass therethrough. Alternatively, an exterior surface of proximally extending circular wall of circular hood having the T-shaped cross-section embodiment may be attached to inner surface 115 at the distal end of first elongate shaft 110. The hood in this embodiment may also define an opening as in the other embodiments.

In FIG. 9, in accordance with an embodiment of the present invention, outer surface 122 of needle 120 may be coaxially aligned with and have a stop collar 930 attached near the distal end of needle 120. Stop collar 930 may include a proximal end 932 and a distal end 933. Distal end 933 of stop collar 930 may have a stair-step configuration to be used to selectively specify the depth of an injection. The orientation of stop collar 930 is controlled by rotating needle 120. In addition, outer surface 122 of needle 120 may be completely and/or partially surrounded by a needle depth control device 940 attached near the distal end of catheter 100. Needle depth control device 940 may include a proximal end 942 and a distal end 943. Proximal end 942 of needle depth control device 940 may have a stair-step configuration (shown in partial phantom line) that is the reciprocal of and facing distal end 933 of stop collar 930. Urging needle 120 distally causes distal end 933 of stop collar 930 to move toward proximal end 942 of needle depth control device 940 and extend needle 120 out past the distal side of hood 910 until distal end 933 of stop collar 930 engages stop mechanism 914. Needle 120 may be rotated in catheter lumen 116 to select how the reciprocal end of stop collar 930 will engage needle depth control device 940.

In FIG. 9, how distal end 933 of stop collar 930 contacts proximal side 942 of needle depth control device 940 to urge needle 120 toward distal end 103 of catheter 100 determines the injection depth, that is, the distance needle 120 may be extended past the distal side of hood 910, may be specified by selecting how the reciprocal ends of stop collar 930 and needle depth control device engage each other. The injection depth may be selected using, for example, but not limited to, a sliding scale, push button selector, and/or dialing mechanism. For example, needle 120 may be rotated within catheter lumen 116 to select the depth based on the orientation of stop collar 930 and needle depth control device 940. As in the previously described embodiments, in the present embodiment, although the predetermined distance may be selected at the proximal end of catheter 100, control of the distance occurs near the distal end of catheter 100.

FIG. 10 is a cross-sectional side view of a portion of the distal end of catheter 100 and is similar to the distal end of first elongate shaft 110 of FIG. 6, in accordance with another embodiment of the present invention. In FIG. 10, first elongate shaft 110 of catheter 100 may include a generally circular hood 1010 having a proximally extending circular wall 1012 (hood 1010 shown as having a generally L-shaped cross-section in the embodiment in FIG. 10) attached at the distal end of first elongate shaft 110. Hood 1010 may form a circumferential ring around distal end 113 of first elongate shaft 110 and hood 1010 may be of sufficient width to prevent hood 1010 from perforating tissue with which it comes in contact. In FIG. 10, hood 1010 may be attached to inner surface 115 of first elongate shaft 110 to form a stop mechanism 1014 with the proximal end of proximally extending circular wall 1012.

In other embodiments of the present invention, hood 1010 maybe formed as an integral part of first elongate shaft 110. Regardless, in FIG. 10, hood 1010 may define an opening 1020 co-axially aligned with and smaller than lumen 116 of catheter 100, but of sufficient size to permit needle 120 to pass therethrough. As such, hood 1010 may extend over and partially close off catheter lumen 116, to act as stop mechanism 1014 to prevent needle 120 from extending beyond a selected depth. In accordance with other embodiments of the present invention, hood 1010 may be attached to outer surface 117 of first elongate shaft 110, but not obstruct catheter lumen 116.

In accordance with other embodiments of the present invention, in FIG. 10, hood 1010 may include a generally circular hood similar to hood 1010 and having a similar proximally extending circular wall so as to have a generally T-shaped cross-section. An interior surface of the proximally extending circular wall may be of sufficient size to fit around and attach to outer surface 117 at the distal end of first elongate shaft 110. The hood in this embodiment may also define an opening co-axially aligned with and smaller than catheter lumen 116, but of sufficient size to permit needle 120 to pass therethrough. Alternatively, an exterior surface of proximally extending circular wall of circular hood having the T-shaped cross-section embodiment may be attached to inner surface 115 at the distal end of first elongate shaft 110. The hood in this embodiment may also define an opening as in the other embodiments.

In FIG. 10, in accordance with an embodiment of the present invention, outer surface 122 of needle 120 may be coaxially aligned with and permanently attached to a third elongate shaft 1040. Third elongate shaft 1040 may include a proximal end 1042 and a distal end 1043 and may extend from the proximal end to near the distal end of needle 120. Urging needle 120 distally may also cause third elongate shaft 1040 to move distally with needle 120. Distal end 1043 of third elongate shaft 1040 may contact stop mechanism 1014 to stop needle 120 from extending any further out past the distal side of hood 1010.

In accordance with the embodiment in FIG. 10, third elongate shaft 1040 and needle 120 move together toward distal end 103 of catheter 100. Distance distal end 1043 of third elongate shaft 1040 is from stop mechanism 1014 may determine the injection depth, that is, the distance needle 120 may be extended past the distal side of hood 1010. However, in accordance with embodiments of the present invention, distal end 1043 may be located farther away from stop mechanism 1014 than the injection depth selected at the proximal. In such a case, distal end 1043 may not contact stop mechanism 1014, but may stop once a selected injection depth is reached. The injection depth may be selected using, for example, but not limited to, a sliding scale (for example, slider 140 and indicia 152 on housing 150 of FIG. 1), a push button selector, and/or a dialing mechanism located at the proximal end of catheter 100. Unlike the previous embodiments, the depth of the injection may be controlled at the proximal end.

FIG. 11 is a cross-sectional side view of a portion of the distal end of catheter 100 and is similar to the distal end of first elongate shaft 110 of FIG. 7, in accordance with another embodiment of the present invention. In FIG. 11, first elongate shaft 110 of catheter 100 may include a flared tip 1110 at the distal end 113 of first elongate shaft 110. Flared tip 1110 may form a circumferential ring around distal end 113 of first elongate shaft 110, and flared tip 1110 may be of sufficient width to prevent flared tip 1110 from perforating tissue with which it comes in contact. In embodiments of the present invention, flared tip 1110 may be formed as an integral part of first elongate shaft 110, or it may be an attached component. Regardless, in FIG. 11, flared tip 1110 may define an opening 1120 co-axially aligned with catheter lumen 116 and of sufficient size to permit a needle 1125 to pass therethrough. Needle 1125 may have a needle tip 1128 disposed at a distal end of needle 1125.

In accordance with the embodiment in FIG. 11, needle 1125 may include a dual lumen design. Specifically, a mandrel 1102, for example, a solid mandrel, and a second tube 1104 may both extend from the proximal end to the distal end of needle 1125. Likewise, needle 1125 may be filled with a material 1106 to hold mandrel 1102 and second tube 1104 in substantially consistent positions relative to each other within needle 1125. Mandrel 1102 may provide the column strength needed to transmit the puncture force to needle tip 1128 from the proximal end of needle 1125. Mandrel 1102 may also help limit and/or prevent second tube 1104 and material 1106 from lengthening due to moisture or tensile effects. In this embodiment, mandrel 1102 may include a metallic material, for example, stainless steel or nickel-titanium alloy and second tube 1104 and material 1106 may each include expansion and contraction resistant material(s), for example, a moisture resistant plastic or polymer.

In accordance with an alternative embodiment of the present invention, mandrel 1102 may be slightly undersized, for example, in at least its diameter, to allow mandrel 1102 to move within material 1106 relative to the rest of the dual lumen.

In FIG. 11, second tube 1104 may define a drug compatible lumen 1107 for the delivery of therapeutics from the proximal end to the distal end of needle 1125. In FIG. 11, material 1106 may include, for example, a co-extrusion material, which may fill all available space between an inner surface of needle 1125 and outer surfaces of mandrel 1102 and second tube 1104.

In FIG. 11, in accordance with an alternative embodiment of the present invention, outer surface 1122 of needle 1125 may be co-axially aligned with and have a stop collar attached near the distal end of needle 1125. In addition, outer surface 1122 of needle 1125 may be completely and/or partially surrounded by a needle depth control device located near the distal end of needle 1125. In this alternative embodiment, the stop collar and needle depth control device may be of any of the previously described designs.

In accordance with an embodiment of the present invention, in FIG. 11, second tube 1104 may have known expansion and contraction characteristics and may be of a shorter length than mandrel 1102. In this embodiment, second tube 1104 may expand as the result of absorbing moisture from a fluid introduced in lumen 1107.

FIG. 12 is a cross-sectional view of the needle 1125 of FIG. 11 along line 12-12, in accordance with an embodiment of the present invention. In FIG. 12, mandrel 1102 and second tube 1104 run in parallel in needle 1125. Second tube 1104 may include an outer wall 1207 and an inner wall 1208, which may define drug compatible lumen 1107. Alternatively, drug compatible lumen 1107 may be present in material 1106 without the need for second tube 1104.

FIG. 13 is a plan view of a catheter 100 including distal end 103, proximal end 104, and shaft assembly 110, in accordance with an embodiment of the present invention. Shaft assembly 110 comprises first elongate shaft 110 having distal end 113, proximal end 114, and inner surface 115 defining lumen 116. Shaft assembly 110 may also include third elongate shaft 120, for example, a needle, slidingly disposed within lumen 116 of first elongate shaft 110. First elongate shaft 110 may also include outer surface 117 extending between proximal end 114 and distal end 113 of first elongate shaft 110. First elongate shaft 110 may have hood 118 attached at distal end 113 thereof. Hood 118 may define an opening co-axially aligned with and in communication with lumen 116 through which third elongate shaft 120 may extend past distal end 113 of first elongate shaft 110.

In FIG. 13, third elongate shaft 120 may have outer surface 122, distal end 123, proximal end 124, and inner surface 125. Distal end 123 of third elongate shaft 120 may form tip 127 having injection port 160 that may be in fluid communication with proximal end 124 of third elongate shaft 120 through lumen 128 defined by inner surface 125 of third elongate shaft 120.

In many applications it may be desirable to set distal end 123 of third elongate shaft 120 in FIG. 1 by a known distance relative to distal end 113 of first elongate shaft 124. In the embodiment of FIG. 13, a depth selection device 1310 may be fixed near proximal end 104 of catheter 100 and on third elongate shaft 120 near proximal end 124 thereof. Depth selection device 1310 may indicate a plurality of injection depth settings for third elongate shaft 120 measured, generally, in millimeters. Depth selection device 1310 will be further described below in relation to FIG. 14.

A physician using catheter 100 in a surgical procedure may move distal end 123 of third elongate shaft 120 a known distance relative to distal end 113 of first elongate shaft 110 to set the desired injection depth. For example, a physician may select the desired injection depth by turning needle 120. The movement of needle 120 may be translated via needle 120 to distal end 123 thereof to set the depth.

In FIG. 13, in accordance with an embodiment of the present invention, third elongate shaft 120 may form point 127 proximate distal end 123 thereof. Third elongate shaft 120 may also define an injection port 160 proximate point 127. A hub 130 may be disposed about third elongate shaft 120 proximate proximal end 124 thereof. Hub 130 may define a proximal port 136, which may be in fluid communication with injection port 160 via an injection lumen 128 that may be defined by third elongate shaft 120.

Catheter 100, in FIG. 13, may be generally referred to as an injection catheter. It is to be appreciated that a catheter in accordance with the present invention may comprise various types of catheters, as listed previously, without deviating from the spirit and scope of the present invention.

FIG. 14 is a cross-sectional view of the catheter of FIG. 13 along line 14-14, in accordance with an embodiment of the present invention. In FIG. 14, injection depth device 1310 includes needle 120 having an indicator 1401 attached to its outer surface 122 proximate proximal end 114 of first elongate shaft 110. A plurality of indicia 1452 may be disposed on a proximal end face 1460 of proximal end 114 of first elongate shaft 110. To select an injection depth, needle 120 may be rotated in either a clockwise or counter clockwise direction to the desired depth as indicated by indicia 152. It will be appreciated that such a mechanism may be used with catheters such as those illustrated in FIGS. 7-9.

A detailed description of embodiments of catheter assemblies that may be used in embodiments of the present invention may be found in co-pending U.S. patent application Ser. No. 09/635,083, filed by the same assignee on Aug. 8, 2000, and entitled "Catheter Shaft Assembly," which is hereby incorporated by reference in its entirety.

The term "therapeutic agent" as used herein may include one or more "therapeutic agents" or "drugs." The terms "therapeutic agents" and "drugs" are used interchangeably herein and may include pharmaceutically active compounds, nucleic acids with and without carrier vectors such as lipids, compacting agents (such as histones), virus (such as adenovirus, adenoassociated virus, retrovirus, lentivirus and α-virus), polymers, hyaluronic acid, proteins, cells and the like, with or without targeting sequences.

Specific examples of therapeutic agents used in conjunction with the present invention may include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources may include adenoviral vectors, herpes simplex vectors, papilloma vectors, adeno-associated vectors, retroviral vectors, and the like. Non-limiting examples of biologically active solutes may include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof. Cells may be of human origin (autologous or allogenic) or may be from an animal source (xenogeneic), genetically engineered if desired to deliver proteins of interest at the insertion site. Any modifications are routinely made by one skilled in the art.

Polynucleotide sequences useful in practice of the invention may include DNA or RNA sequences having a therapeutic effect after being taken up by a cell. Examples of therapeutic polynucleotides may include anti-sense DNA and RNA; DNA coding for an anti-sense RNA; or DNA coding for tRNA or rRNA to replace defective or deficient endogenous molecules. The polynucleotides may also code for therapeutic proteins or polypeptides. A polypeptide is understood to be any translation product of a polynucleotide regardless of size, and whether glycosylated or not. Therapeutic proteins and polypeptides may include as a primary example, those proteins or polypeptides that can compensate for defective or deficient species in an animal, or those that act through toxic effects to limit or remove harmful cells from the body. In addition, the polypeptides or proteins that may be injected, or whose DNA can be incorporated, may include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin-like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which may be provided as polypeptides or as DNA encoding these polypeptides, include monocyte chemoattractant protein ("MCP-1"), and the family of bone morphogenic proteins ("BMP's"). The known proteins may include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins may be provided as homodimers, heterodimers, or combinations thereof, alone or together with other molecules. Alternatively or, in addition, molecules capable of inducing an upstream or downstream effect of a BMP may be provided. Such molecules may include any of the "hedgehog" proteins, or the DNA's encoding them.

Although the present invention has been disclosed in detail, it should be understood that various changes, substitutions, and alterations may be made herein, the present invention is intended to cover various modifications and equivalent arrangements. Other examples are readily ascertainable from the above description by one skilled in the art and may be made without departing from the spirit and scope of the present invention as defined by the following claims.

What is claimed is:

1. An injection catheter comprising:
   a first elongated shaft having a distal end and a proximal end and a first lumen extending therebetween;
   a needle with a proximal end and a distal end and a needle lumen extending therebetween, the needle disposed within the first lumen of the elongated shaft and extending from a proximal end of the catheter to a distal end of the catheter;
   a stop collar disposed within the first lumen of the first elongated shaft near the distal end of the needle; the stop collar having a portion thereon configured to prevent lateral movement of the stop collar within the first elongated shaft;
   a first set of threads located on the needle; and
   a second set of threads located on the stop collar;
   wherein rotation of the needle within the first elongated shaft causes longitudinal movement of the stop collar relative to the needle within the first elongated shaft, the positioning of the stop collar within the first elongated shaft controlling a variable extent to which the needle may be extended beyond the distal end of the first elongated shaft.

2. The injection catheter of claim 1, wherein the portion of the stop collar configured to prevent lateral movement comprises:
   a plurality of outwardly extending longitudinal protrusions located on the stop collar; and a plurality of grooves in an inner surface of the elongated shaft to slidingly receive the plurality of outwardly extending longitudinal protrusions.

3. The injection catheter of claim 1 wherein the first elongated shaft is made of a low friction material.

4. The injection catheter of claim 1 wherein the first elongated shaft comprises polytetrafluoroethylene.

5. The injection catheter of claim 1 wherein the first elongated shaft is reinforced with a braid.

6. An injection catheter comprising:
- a first elongated shaft having a distal end and a proximal end and a first lumen extending therebetween;
- a needle with a proximal end and distal end and a needle lumen extending therebetween, the needle disposed within the first lumen of the first elongated shaft and extending from a proximal end of the catheter to a distal end of the catheter;
- a stop collar disposed within the first lumen of the first elongated shaft near the distal end of the needle; the stop collar being longitudinally slidable and rotationally fixed within the first elongated shaft;
- a first set of threads located on the needle; and
- a second set of threads located on the stop collar;
- wherein rotation of the needle within the first elongated shaft causes longitudinal movement of the stop collar relative to the needle within the first elongated shaft, the positioning of the stop collar within the first elongated shaft controlling a variable extent to which the needle may be extended beyond the distal end of the first elongated shaft.

7. The injection catheter of claim 6 further comprising:
- a plurality of outwardly extending longitudinal protrusions located on the stop collar; and
- a plurality of grooves in an inner surface of the first elongated shaft to slidingly receive the plurality of outwardly extending longitudinal protrusions.

* * * * *